United States Patent
Rivera et al.

(10) Patent No.: US 9,012,203 B2
(45) Date of Patent: Apr. 21, 2015

(54) MICROFLUIDIC DEVICE, SYSTEM, AND METHOD FOR CONTROLLED ENCAPSULATION OF PARTICLES OR PARTICLE CLUSTERS

(75) Inventors: Florence Rivera, Meylan (FR); Jean Berthier, Meylan (FR); Sophie Le Vot, Le Pont de Claix (FR)

(73) Assignee: Commissariat a l'Energie Atomique, Paris (FR)

( * ) Notice: Subject to any disclaimer, the term of this patent is extended or adjusted under 35 U.S.C. 154(b) by 1165 days.

(21) Appl. No.: 12/465,112

(22) Filed: May 13, 2009

(65) Prior Publication Data

US 2009/0286298 A1    Nov. 19, 2009

(30) Foreign Application Priority Data

May 13, 2008    (FR) ...................................... 08 02578

(51) Int. Cl.
*C12M 3/00*    (2006.01)
*C12N 11/04*    (2006.01)

(52) U.S. Cl.
CPC ...................................... *C12N 11/04* (2013.01)

(58) Field of Classification Search
CPC ...... C12M 21/08; C12M 23/16; C12M 25/16; B01L 3/502769; B01L 3/502784; B01L 2200/0673
USPC ................ 435/288.5, 293.1, 182, 403, 286.5; 422/502–505, 93, 73, 82
See application file for complete search history.

(56) References Cited

U.S. PATENT DOCUMENTS

| | | | |
|---|---|---|---|
| 6,524,456 B1* | 2/2003 | Ramsey et al. | 204/450 |
| 7,268,167 B2* | 9/2007 | Higuchi et al. | 516/9 |
| 2004/0072278 A1* | 4/2004 | Chou et al. | 435/29 |
| 2006/0051329 A1 | 3/2006 | Lee et al. | |
| 2007/0009668 A1 | 1/2007 | Wyman et al. | |

FOREIGN PATENT DOCUMENTS

WO    WO 2005/103106 A    11/2005

OTHER PUBLICATIONS

International Search Report for French Application No. 08/02578, filed May 13, 2008.
Sugiura S et al: "Size control of calcium alginate beads containing living cells using micro-nozzle array"; Jun. 1, 2005; Biomaterials, Elsevier Science Publishers BV., Barking, GB, pp. 3327-3331; XP004684998.

\* cited by examiner

*Primary Examiner* — William H Beisner
(74) *Attorney, Agent, or Firm* — Alston & Bird LLP

(57) ABSTRACT

A microfluidic device for controlled encapsulation of particles of sub-millimetric dimensions, or clusters of such particles, the device comprising: a first duct for delivering a first liquid phase containing particles for encapsulating in suspension; a second duct for conveying a flow of a second liquid phase that is immiscible with said first liquid phase; the first duct opening out into the second duct and forming a fluidic junction therewith; at least one microfluidic duct for discharging the first liquid phase flowing in said first duct and provided with a mouth located upstream from said junction and liable to be obstructed, at least in part, by a particle in suspension, thereby causing pressure to rise in the first duct. The invention also provides a microfluidic system including such a device, and a method of encapsulation based on using such a device.

4 Claims, 4 Drawing Sheets

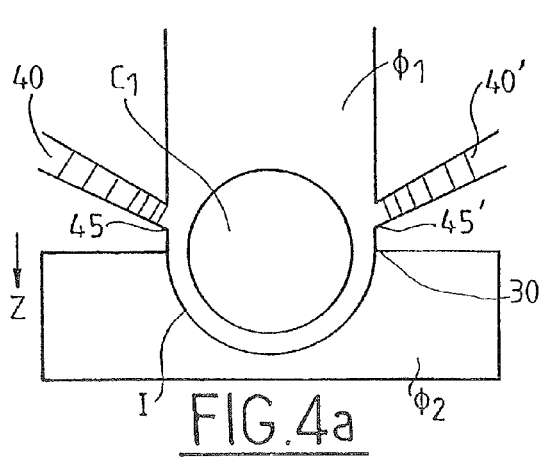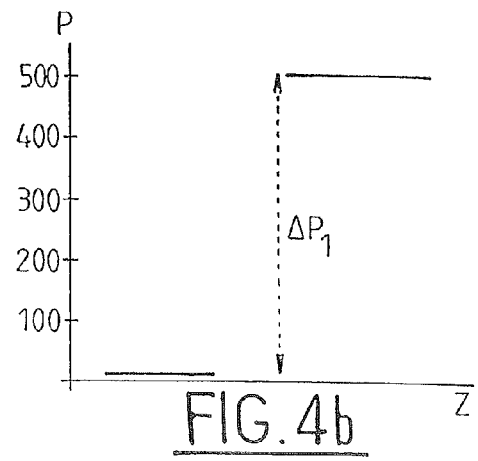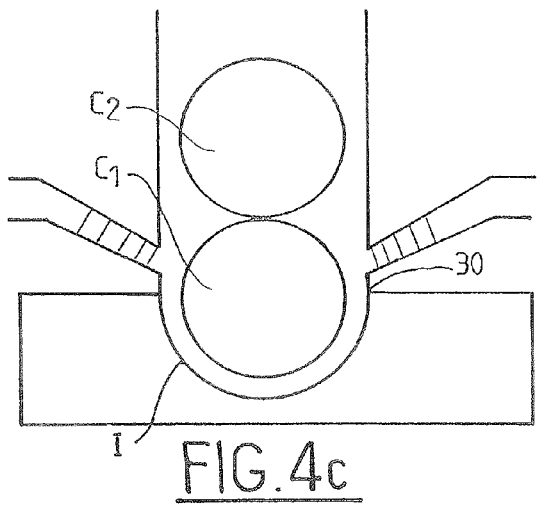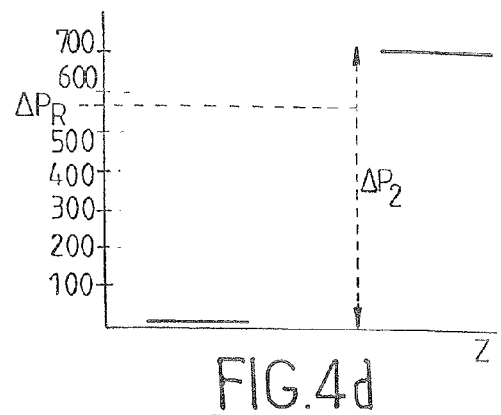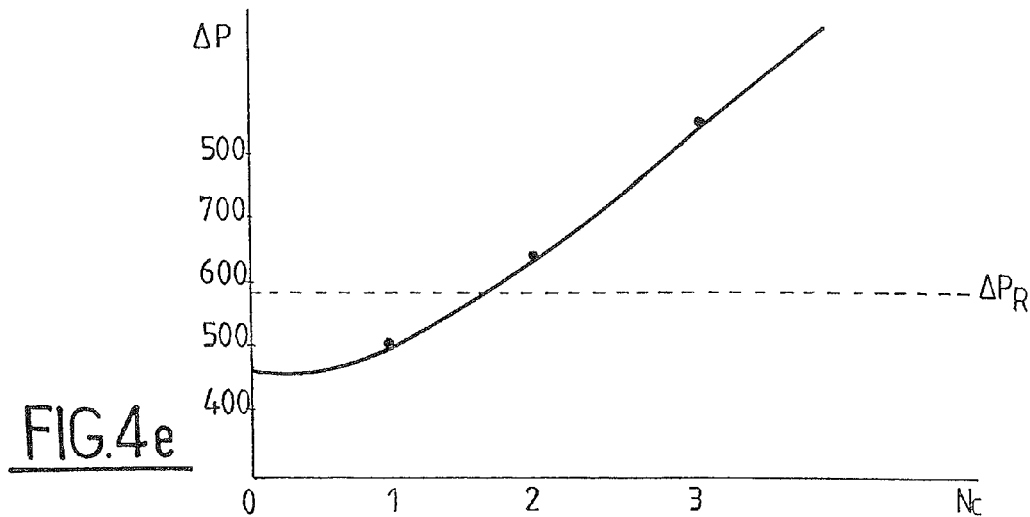

MICROFLUIDIC DEVICE, SYSTEM, AND METHOD FOR CONTROLLED ENCAPSULATION OF PARTICLES OR PARTICLE CLUSTERS

CROSS REFERENCE TO RELATED APPLICATION

This application claims priority from French Application No. 08 02578, filed May 13, 2008, which is hereby incorporated herein in its entirety by reference.

FIELD OF THE INVENTION

The invention relates to a microfluidic device, system, and method for controlled encapsulation of particles of sub-millimetric dimensions, or clusters of such particles. The invention is suitable more particularly for encapsulating cells, in particular human cells, or clusters of cells, such as islets of Langerhans.

BACKGROUND OF THE INVENTION

Cellular encapsulation is a technique that consists in immobilizing cells or clusters of cells in microcapsules so as to protect them from immune system attacks after being transplanted. The capsules need to be sufficiently porous to allow entry of molecules of low molecular weight that are essential for the metabolism of the encapsulated cells, such as nutrient molecules, oxygen, etc., while simultaneously preventing entry of substances of high molecular weight, such as antibodies or cells of the immune system. This selective permeability of the capsules is thus designed to prevent direct contact between the encapsulated cells from the donor and cells of the immune system of the recipient of the transplant, thereby making it possible to limit the doses of immunodepressive treatment used with transplantation, since said immunodepressive treatment presents severe side effects. In addition to their selective permeability, the capsules that are produced must be biocompatible, mechanically strong, and of size that matches the article to be encapsulated.

Amongst the multiple applications of encapsulation, mention can be made of islets of Langerhans, clusters of fragile cells that are situated in the pancreas and that are constituted by several types of cell including β cells that regulate glycemia in the body by producing insulin. Encapsulating these islets is an alternative to conventional cell therapies (e.g. pancreas or islet transplantation) used for treating insulin-dependent diabetes, an auto-immune disease in which the immune system destroys its own insulin-producing β cells.

The main known methods of encapsulation make use of either:
- a coaxial jet of air or liquid, the resulting capsules having size that lies in the range 400 micrometers ($\mu m$) to 800 $\mu m$ (although the mean size of the capsules produced lies closer to the range 600 $\mu m$ to 800 $\mu m$ than to 400 $\mu m$: see Zimmermann, "Fabrication of homogeneously cross-linked, functional alginate microcapsules validated by NRM-, CLSM-, and AFM-imaging", Biomaterials, 2003, 24: pp. 2083-2096; or
- a potential difference, which is the encapsulation technique in the most widespread use when the priority is to reduce the size of the capsules (capsule size then lying in the range 200 $\mu m$ to 800 $\mu m$); see Goosen, "Electrostatic droplet generation for encapsulation of somatic tissue: assessment of high-voltage power supply", Biotechnol. Prog., 1997, 13, pp. 497-502; or else
- a vibration technique that presents the drawback of sometimes being limited by the viscosities of the solutions being used; see Seifert, "Production of small, monodispersed alginate beads for cell immobilization", Biotechnol. Prog., 1997, 13, pp. 562-568.

Those techniques known in the prior art include certain drawbacks:
- the size of the capsule is not necessarily appropriate for the size of the cells/islets that are to be encapsulated;
- the dispersion of capsule size increases with decreasing drop size; and
- the capsules produced are not necessarily spherical, thereby leading to a lack of reproducibility.

In addition to those problems, most present encapsulation techniques do not provide any way of controlling the number of cells or cell clusters that are contained in each droplet. The number of cells or clusters that are encapsulated is determined only statistically by adjusting the concentration of the suspension of cells (or clusters) in the polymer solution acting as the encapsulation matrix (this concentration depends on the size of the particles for encapsulation and on the size desired for the capsules). Conventional systems thus produce a very large number of empty capsules together with capsules containing varying numbers of cells or clusters.

The main drawback of empty capsules is to increase the total cell volume that needs to be transplanted and to prevent them being transplanted into zones that would be particularly suitable for tissue revascularization, which is essential to avoid necrosis of the encapsulated cells, since they need to be close to the blood network in order to be fed with nutrients and oxygen. For example, for treatment of type 1 diabetes, a reduction in the total volume of capsules for transplanting would make it possible to implant encapsulated islets in the liver or the spleen, regions that are more favorable for revascularization than the peritoneal cavity where capsules are conventionally implanted for questions of steric hindrance.

When the capsules contain varying numbers of cells or clusters, there is a risk of the cells or clusters projecting from the surface of the capsule, thereby running the risk of triggering an immune reaction in which the graft is rejected. This problem is made worse when the size of the capsule is a close fit to the size of the article to be encapsulated.

To solve the drawbacks of the above-mentioned conventional techniques, encapsulation devices and methods have been proposed that are based on microfluidic techniques. See for example:
- Workman et al., "Microfluidic chip-based synthesis of alginate microspheres for encapsulation of immortalized human cells", Biomicrofluidics, 2007, 1. That article describes a method of fabricating capsules having a diameter lying in the range 80 $\mu m$ to 400 $\mu m$ approximately, by means of a so-called "hydrodynamic focusing" effect; and
- Sugiura et al., "Size control of calcium alginate beads containing liver cells using micronozzle array", Biomaterials, 2005, 26: pp. 3327-3331. In the method described in that publication, capsules of size lying in the range 50 $\mu m$ to 200 $\mu m$ are formed by injecting alginate into an oily phase through "micronozzles" having a diameter of 30 $\mu m$.

Those techniques provide better control over capsule size, and said size is reduced compared with using conventional techniques; however the number of particles (cells or clusters) per capsule remains highly variable.

At present, the only technique known to the inventors that enables isolated particles to be encapsulated relies on the combined use of microfluidics and of optical tweezers enabling a cell contained in the aqueous phase to be moved towards the water/oil interface at a T-junction. This technique also presents the advantage of producing a capsule of size that is of the same order of magnitude as the size of the encapsulated cell. Nevertheless, it does not make it possible to achieve encapsulation rates that are sufficient to make application thereof viable outside the field of scientific research.

SUMMARY OF THE INVENTION

The invention seeks to solve at least some of the drawbacks of the prior art.

In particular, the invention seeks to enable cells or cell clusters to be encapsulated in numbers that are controlled and reproducible. Advantageously, the invention enables capsules to be fabricated of a size that is well matched to the numbers of cells or clusters they contain, while avoiding producing capsules that are empty.

The device of the invention is of the microfluidic type, it presents a structure that is simple, and it can be made at low cost by conventional microfabrication techniques.

More precisely, the invention provides a microfluidic device for controlled encapsulation of particles of sub-millimetric dimensions, or clusters of such particles, the device comprising: a first microfluidic duct for delivering a first liquid phase containing in suspension particles or particles clusters for encapsulating; a second microfluidic duct for conveying a flow of a second liquid phase that is immiscible with said first liquid phase; the first duct opening out into the second duct and forming a fluidic junction therewith; at least one discharge microfluidic duct for discharging the first liquid phase flowing in said first duct, being provided with a mouth disposed upstream from said junction and being suitable for being obstructed, at least in part, by a particle or particle cluster in suspension, thereby causing pressure to rise in the first duct; whereby particles or particle clusters entrained by said suspension along said first duct are liable to accumulate at said junction, being trapped at an interface between the two immiscible liquid phases, until they are injected into said second duct by the pressure rise caused by the mouth(s) of said discharge duct(s) being obstructed.

Advantageously, the device of the invention may include at least one pair of microfluidic discharge ducts disposed on either side of said first duct.

More precisely, the device may have only a single discharge duct or only a single pair of discharge ducts.

In a first embodiment, the section of the mouth of said encapsulation duct(s) and the distance of the mouth(s) from the junction, and also the section of the first duct, may be selected in such a manner that the arrival of a single particle or particle cluster at said junction induces in the first duct a pressure rise that is sufficient to enable said particle or particle cluster to be injected into the second duct.

In a second embodiment, the section of the mouth(s) of said discharge duct(s) and the distance of the mouth(s) from the junction, together with the section of the first duct, may be selected in such a manner that a pressure sufficient for enabling a particle or particle cluster to be injected into the second duct is not reached until a predetermined number of particles or particle clusters is trapped at the junction by said interface between the two immiscible liquid phases, said predetermined number being greater than 1, and preferably lying in the range 2 to 10.

In a third embodiment, the device may include at least two discharge ducts or at least two pairs of discharge ducts having mouths situated at different distances from said junction, in which the section(s) of the mouths of said discharge ducts and the distance(s) of the mouths from the junction, and the section of the first duct, are selected in such a manner that a pressure sufficient for enabling a particle or particle cluster to be injected into the second duct is reached only when said at least two ducts or at least two pairs of ducts are obstructed, thereby making it possible to ensure that a plurality of particles or particle clusters are injected simultaneously.

In a fourth embodiment, the device may include an array of micro-pillars at said or each mouth of said discharge duct(s).

The device may include an array of micro-pillars at the fluidic junction between the first and second ducts.

Said fluidic junction may be a T-junction, the first and second ducts forming between them an angle lying in the range 60° to 90°, preferably in the range 80° to 90°, and even more preferably, substantially equal to 90°.

In a variant, said fluidic junction may be a microfluidic flow focusing junction.

In variant embodiments of the invention:
Said first and second ducts may present sections lying in the range 110% to 130% of the diameter d of the article to be encapsulated; said discharge duct(s) present sections of the order of 30% to 60% of the section of the first duct; and the distance(s) of the mouth(s) of said discharge duct(s) or pair(s) of discharge ducts from said junction lie(s) in the range 10% to 50% of the diameter of the article to be encapsulated.
Said ducts may be constituted by furrows etched or molded in a substrate.
Alternatively, the device may present a three-dimensional structure and be constituted by a stack of molded or etched planar substrates, with the first duct passing substantially perpendicularly through said substrate, while the second duct and the discharge duct(s) are formed at interfaces between substrates and parallel thereto.
The dimensions of said ducts may be adapted to enable cells or bacteria to be encapsulated.

The invention also provides a microfluidic system for controlled encapsulation of particles of sub-millimetric dimensions or clusters of such particles, the system comprising: a device as described above; injector means for injecting into the first duct of said device a first liquid phase containing in suspension particles of sub-millimetric dimensions or clusters of such particles for encapsulating, said liquid phase also containing at least one encapsulation agent; discharge means for discharging the first liquid phase flowing in said first duct via said discharge duct(s); and injector means for injecting into the second duct of said device a second liquid phase that is immiscible with said liquid phase; wherein said injector means for injecting the first and second liquid phases, and said discharge means for discharging the first liquid phase are adapted to enable a stable interface to be formed between the two immiscible liquid phases at said junction, and to enable said interface to rupture in the event of one or more of said discharge ducts being obstructed.

Such a system may also include a gelling unit connected to said second duct downstream from said junction, said unit being adapted to: receive as input said second liquid phase containing in suspension the particles or particle clusters injected into said second duct and surrounded in film constituted by the first liquid phase; and cause the encapsulation agent contained in said film to gel so as to constitute capsules containing said particles or particle clusters.

The invention also provides a microfluidic method for controlled encapsulation of sub-millimetric particles or clusters of such particles, the method comprising the steps consisting in: injecting into the first duct of a device as described above, a first liquid phase containing in suspension particles or particle clusters for encapsulating, said liquid phase also containing at least one encapsulation agent; discharging the liquid phase flowing in said first duct through said discharge duct(s); and injecting into the second duct of said device a second liquid phase that is immiscible with said first liquid phase; the pressure that which the first and second liquid phases are injected and the discharge flow rate of the first liquid phase being selected in such a manner as to enable a stable interface to be formed between the two immiscible liquid phases at said junction, and to enable said interface to be ruptured and a controlled number of particles or particle clusters to be injected into said second duct in the event of one or more of said discharge ducts being obstructed.

The method may also include a step of gelling the encapsulation agent contained in a film constituted by said first liquid phase surrounding the particles or particle clusters injected into said second duct in order to form solid-walled capsules enclosing said particles or particle clusters.

Said particles may be selected from cells, in particular human cells, and bacteria. In particular, the cells may be pancreatic cells, such as β cells, or more generally cells that secrete hormones, proteins, or any other substance of therapeutic interest. The cells may also be stem cells. By way of example, the cell clusters may be islets of Langerhans.

BRIEF DESCRIPTION OF THE DRAWINGS

Other characteristics, details, and advantages of the invention appear on reading the following description made with reference to the accompanying drawings given by way of example, and in which:

FIGS. 4a to 4e show the distribution of hydraulic pressure in the FIG. 1 device;

DETAILED DESCRIPTION OF THE INVENTION

Figure 1:
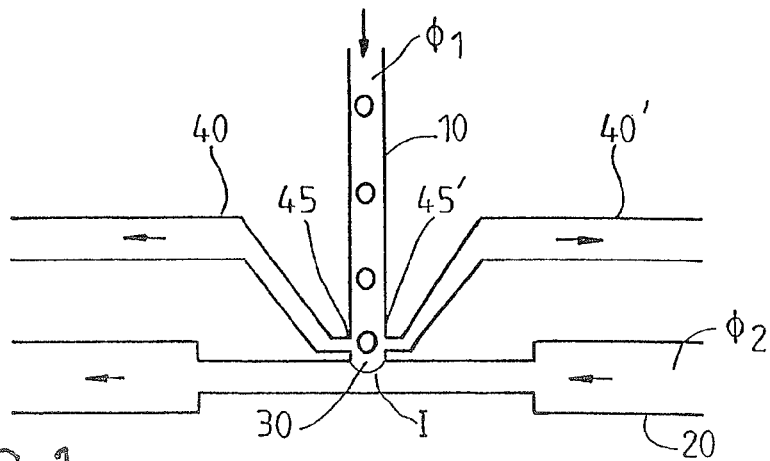
FIGS. 1 to 3 and 8 are schematic diagrams showing four different embodiments of a device of the invention.

The microfluidic device of the invention uses two immiscible phases: for example an aqueous first phase referenced $\phi_1$ in the figures, and an oily type second phase $\phi_2$. By way of example the first phase may be constituted by a biological buffer or a physiological serum; it contains in suspension cells or clusters of cells (C in the figures) for encapsulating, and in solution an encapsulation agent such as an alginate hydrogel, chitosan, carrageenans, agarose gels, polyethylene glycol (PEG), or any other suitable polymer.

The second phase may be a vegetable oil (e.g. sunflower oil), a mineral oil, silicone, a perfluorinated solvent, etc.

It is not absolutely essential for the first phase to be of the aqueous type and the second of the oily type. What is essential is that these two phases should be immiscible, and except in particular applications, that the first phase should enable cells or cell clusters to survive.

The device comprises first and second main microfluidic ducts given references 10 and 20 that form a T-junction 30. Secondary ducts 40, 40', 50, 50' depart from the first duct 10 close to the junction 30.

The first duct 10 is fed with the aqueous phase $\phi_1$ and it opens out into the second duct 20 that is fed with the oily phase $\phi_2$; the two ducts thus form a fluidic T-junction. The term "T-junction" is known in the field of microfluidics and should not be interpreted too strictly. It is not essential for the two ducts to form between them an angle that is exactly equal to 90°. By way of example, the angle may lie in the range 60° to 90°, and preferably in the range 80° to 90°, with values closer to 90° being particularly preferred.

Since the two liquid phases $\phi_1$ and $\phi_2$ are immiscible, an interface I forms at the junction 30. The aqueous phase $\phi_1$ is prevented by said interface from flowing into the second duct, and it flows away via the secondary ducts 40, 40', 50, 50'. The pressures and the flow rates of the two liquid phases are dimensioned in such a manner that the interface I remains stable by virtue of equilibrium between said pressures and the tension at the interface.

The secondary or discharge ducts 40, 40', 50, 50' present respective mouths open to the channel 10 and of section that is smaller than the section of the main ducts 10 and 20, and they do not allow the cells C to pass therethrough. The particles (cells or clusters) delivered by the liquid first phase $\phi_1$ therefore remain trapped at the interface I, while said liquid phase is discharged via the secondary ducts. This continues until said particles obstruct the mouths of said secondary ducts; this causes the pressure to rise and leads to the interface I breaking, with one or more particles being injected into the second duct.

More precisely, obstructing the discharge ducts generates a transient pressure rise that causes a droplet of the first liquid phase to be injected into the second duct, which droplet contains one or more particles. The size of the droplet, referenced K in the figures, matches the size of the cells or the cluster it contains: it is possible to consider the droplet K as being a fine liquid film surrounding one or more particles. This liquid film constitutes the precursor of the capsule that is to be formed, in a manner that is itself known, by gelling the encapsulation agent (e.g. alginate) that is in solution in the first liquid phase.

Forming droplets in an immiscible liquid phase by means of a T-junction between two microfluidic ducts is known in the prior art. See for example the article by T. Thorsen et al., "Dynamic pattern formation in a vesicle-generating microfluidic device", Physical Review Letters, 2001, 86(18): pp. 4163-4166.

The device of the invention makes it possible to control accurately the number of particles (cells or clusters) that are injected at the same time, and thus that are contained in a given capsule. This can be understood with the help of three examples.

In the embodiment of FIG. 1, two secondary discharge ducts 40, 40' are provided symmetrically on either side of the first duct 10 in the immediate proximity of the junction 30. The section of the mouths 45, 45' of said discharge ducts 40, 40' and their distance from the junction 30, together with the section of the first duct, are selected so that the arrival of a single particle at said junction suffices to obstruct said discharge ducts, thereby generating a significant pressure rise so as to enable said particles to be injected into the second duct. In other words, the particles are injected one by one as soon as they reach the interface I. Naturally, for this to happen, it is necessary for the particles to be spaced apart sufficiently in the first liquid phase to ensure that they reach the junction individually at not in groups.

FIG. 1 is a two-dimensional view of the device, but in reality the ducts present finite depth. This depth naturally needs to be taken into account when dimensioning the sections of said ducts.

The depths of the various ducts of the device may be uniform or different. As a general rule, the terminal portion of the first duct 10 needs to match the diameter of the particles for encapsulating so as to enable the discharge ducts 40, 40' to be obstructed; in contrast, the second duct 20 and the particle feed ducts situated upstream from said duct 10 (and not shown) may present greater depth in order to reduce head losses and limit shear on the particles. This is particularly advantageous with particles of very small dimensions (micrometric, or even sub-micrometric) such as bacteria.

Figure 2:
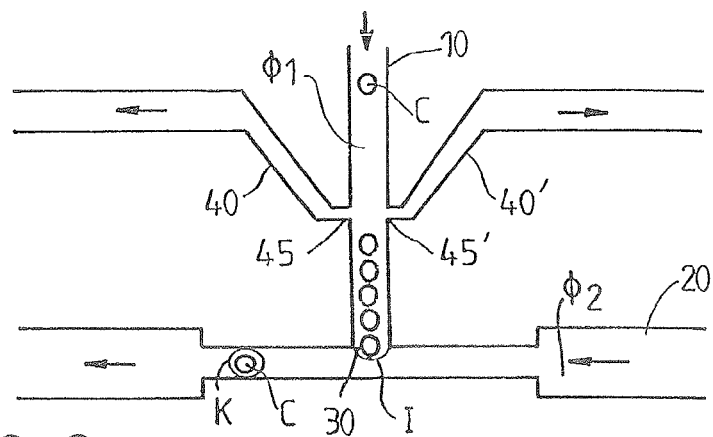

In the embodiment of FIG. 2, the discharge ducts 40, 40' (or more precisely their mouths 45, 45') are situated at a greater distance from the junction 30. In this way, in order to obstruct said discharge ducts, it is necessary for a plurality of particles C to be trapped at the interface I. The figure shows an example in which five particles are already stacked in the first duct 10 and are held in said duct 10 by surface tension at the $\phi_1$-$\phi_2$ interface, without the secondary ducts 40, 40 becoming obstructed. In contrast, the arrival of a sixth particle will cause an obstruction and thus a rise of the pressure in the first duct that will in turn cause the first particle of the line or "queue" to be injected into the second duct. In this example also, the particles are injected one by one.

Compared with the embodiment of FIG. 1, the advantage of this embodiment is that it is technologically easier to make, particularly when it is desired to encapsulate isolated cells or clusters of small dimensions: under such circumstances, implementing the first example would require the secondary ducts to be fabricated very close to the junction 30.

A device of the type shown in FIG. 2 can also be used for injecting a plurality of particles simultaneously: everything depends on the dimensioning of the ducts and on the injection (and possibly discharge) pressures of the two liquid phases.

This second embodiment is also more suitable when the particles for injection are polydisperse. Nevertheless, under such circumstances, control over the number of particles contained in each capsule is less accurate than when the particles suspension is monodisperse, however the size of the capsules remains monodisperse, and if capsule formation occurs, the capsules will necessarily contain cells and will not be empty.

Furthermore, this second embodiment makes it possible to use a main duct that is relatively large even for encapsulating particles of small dimensions, thereby reducing the Laplace pressure and thus the potentially harmful compression forces that act on said particles.

As mentioned above, the distance between the mouths 45, 45' of the discharge ducts and the junction 30 is not the only parameter that needs to be taken into consideration: the sections of said mouths and of the first duct also need to be dimensioned appropriately so as to ensure that the discharge ducts do not become obstructed in sufficiently complete manner until the $(N+1)^{th}$ particle arrives, where N is accurately determined when designing the device. This dimensioning is performed by assuming that the injection pressures and the surface tensions of the two liquid phases, and also the size of the particles for encapsulation, are all known.

Figure 3:
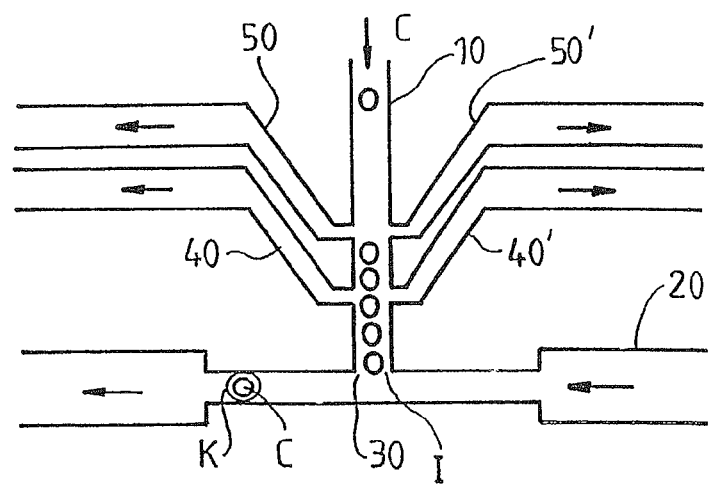

In a third embodiment, shown in FIG. 3, two pairs of discharge ducts (40, 40' and 50, 50') are provided at different distances from the junction 30. The device is dimensioned so that obstructing only one pair of ducts is not sufficient for causing the fluid interface I to rupture. For example, as shown in the figure, the first pair of ducts 40, 40' (the pair closer to the junction) is obstructed when four particles C have accumulated at the junction, while the second pair of ducts 50, 50' is not obstructed until the arrival of the sixth cell.

When said sixth cell arrives, the pressure rise in the first duct reaches a level that is sufficient to rupture the interface I, and the particles C begin to be injected into the second duct 20. The mouths of the second discharge ducts are thus disengaged, however the mouths of the first ducts continue to be obstructed. As a result some pressure continues to remain in the duct 10; this pressure, on its own, is not sufficient for breaking the fluid interface I, however it is sufficient to sustain a rupture that has already occurred. Said interface therefore cannot reform until the mouths of all of the evacuation ducts have been cleared, i.e. after three particles have been injected into the duct 20.

This third embodiment is thus suitable for encapsulating simultaneously a controlled number of cells or cell clusters that is greater than 1 and that preferably lies in the range 1 to 10.

Figure 8:
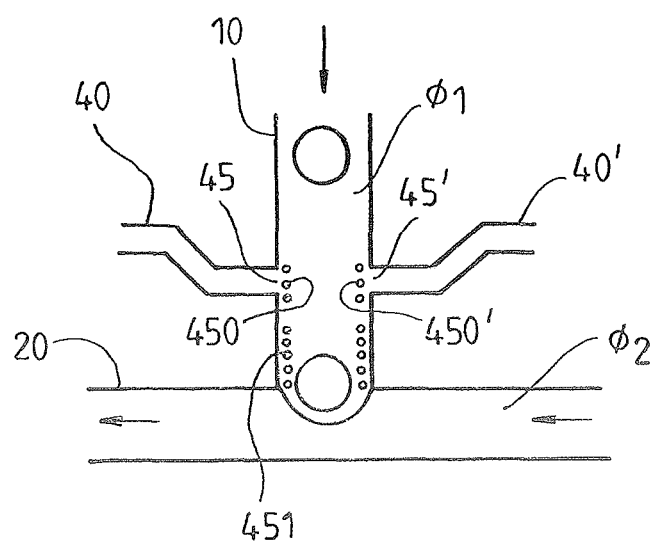

In a fourth embodiment shown in FIG. 8, arrays of micro-pillars 450, 450' are provided at the mouths 45, 45' of the evacuation ducts 40, 40'. In the absence of cells, the flow of the phase $\phi_1$ filters through the gaps between the pillars and discharges into the two lateral discharge ducts 40 and 40'. When one or more cells come to rest in the vicinity of the interface with the phase $\phi_2$, the hydraulic resistance of the phase $\phi_1$ increases suddenly and pressure is exerted on the stationary cell(s). By appropriately dimensioning the head losses between the pillars and in the discharge ducts, this pressure rise is sufficient to eject one or more cells held captive in droplets into the phase $\phi_2$. The advantage of the pillars lies in head losses being determined accurately and also in controlled trapping of cells between the pillars. Since the cells are somewhat deformable, they become lodged in the gaps between the pillars, so they are located accurately. If D designates the diameter of the cells for encapsulation, then the diameter of the pillars preferably lies in the range D/5 to D/3, with the spacing between two pillars in the direction of the duct 10 preferably lying in the range 2D/3 to 4D/5.

As shown in FIG. 8, an additional array of micro-pillars 451 can also be provided at the junction 30 between the ducts 10 and 20 for the purpose of stabilizing the cells and holding them stationary in very accurate manner. This additional array 451 can also be used independently of the arrays 450 and 450' located at the mouths of the discharge ducts.

In the four embodiments shown in FIGS. 1 to 3 and 8, the discharge ducts are arranged in pairs, in exactly symmetrical manner about the first duct 10. This is not really essential, and asymmetrical discharge ducts, or even ducts disposed on one side only of the first duct can be used. Nevertheless, an at least approximately symmetrical arrangement of the discharge ducts is preferable in order to avoid particles that are flowing in the first duct being sucked into the discharge ducts disposed on a single side, thereby obstructing them in untimely manner.

The physical dimensions of a device of the kind described above depend on the intended application, and in particular on the size of the particles to be encapsulated. By way of example, isolated cells may have diameters of the order of a few micrometers, whereas clusters of the Langerhans islet type may reach or even exceed a diameter of 500 μm. Nevertheless, as a general rule, the device needs to be of the microfluidic type: this means that the transverse dimensions of the ducts need to lie in the range a few micrometers or tens of micrometers to one millimeter or at most a few millimeters.

FIGS. 4a and 4c show an enlargement of the region immediately adjacent to the junction 30 of a device of the invention. The gray levels represent pressure values in the two liquid phases $\phi$ and $\phi_2$. The graphs if FIGS. 4b and 4d show the pressure differences $\Delta P_1$, $\Delta P_2$ across the interface I for the situations shown in FIGS. 4a and 4c respectively.

In the situation of FIGS. 4a and 4b, a single particle C1 is present at the interface I between the two liquid phases. The mouths of the discharge ducts are situated at a distance from the junction that is less than the diameter of the particle; nevertheless, said discharge ducts are obstructed in part only, since sufficient space remains at the sides of the main duct to allow the first liquid phase to flow. This example shows clearly that the distance between the mouths and the junction is only one of the parameters that need to be taken into account when dimensioning the device.

The arrival of a second particle C2 (FIG. 4c) constitutes an additional obstacle to discharging the liquid; consequently, the pressure difference across the interface increases and reaches a value $\Delta P_2$ that is greater than the critical value $\Delta P_R$ that leads to the interface I rupturing. At least one of the two particles is therefore injected into the second duct 20. More exactly: both particles are injected if the value of $\Delta P_1$ is sufficient to maintain the rupture of the interface; otherwise, only one particle C1 (the first in line) is injected, and then a stable interface reforms immediately afterwards.

FIG. 4e shows how the value of the pressure difference $\Delta P$ depends on the number of particles $N_C$ at the interface I: the continuous line is merely to guide the eye. It can be seen that $\Delta P$ is not equal to zero even when there are no particles at the junction: this value $\Delta P(0)$ is equal to the surface tension at the interface.

The pressure difference $\Delta P_R$ that causes the interface to rupture is given by:

$$\Delta P_R = \gamma_{12}\left(\frac{1}{w} + \frac{1}{d}\right)$$

where $\gamma_{12}$ is the interface tension between the two liquid phases, while w and d are respectively the width and the depth of the first duct, assumed to be of rectangular section.

The pressure values on the graphs of FIGS. 4b, 4d, and 4e are given in Pascals (Pa).

The embodiments of FIGS. 1 to 3 and 8 relate to a device having planar geometry, of the microfluidic chip type.

Such a device can be fabricated on a substrate of silicon, silica, or glass, using conventional photolithographic techniques and etching of the kind used in microelectronics. On silicon, this technology has the advantage of being very accurate (of micrometer order) and of presenting few limitations on etching depths and on pattern widths.

In a variant, the device may be made by molding a plastics material (in particular polydimethylsiloxane—PDMS) using a "master", which is itself made by photolithography.

As a general rule, a wide variety of materials can be suitable for making a device of the invention. Preferably, these materials need to be capable of being sterilized, in particular if the device is for use in fabricating implantable capsules.

The device may also be made in a three-dimensional form, in which the microfluidic inlets and outlets do not all lie in the same plane. Under such circumstances, capsule formation is due not only to the local pressure rise induced by obstructing secondary discharge ducts, but also to the sedimentation force on the cells or cell clusters due to the force of gravity.

Figure 5:
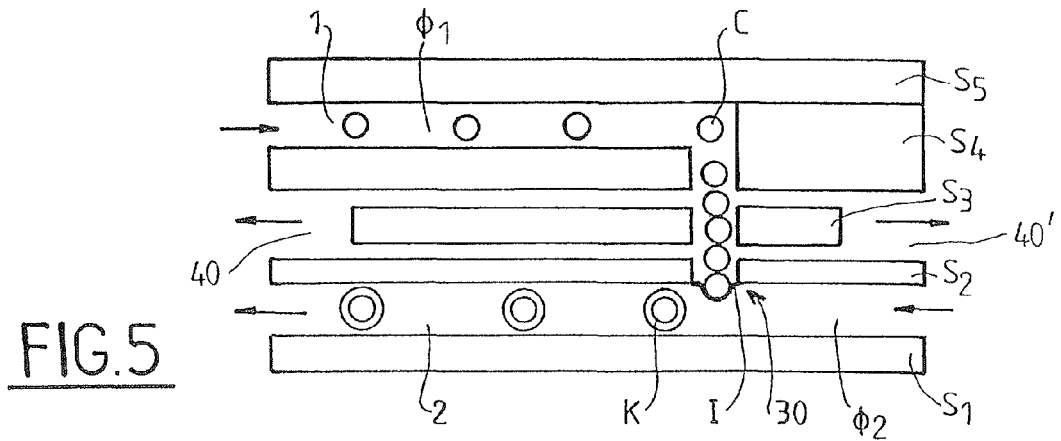
FIG. 5 shows a fifth embodiment of the device of the invention.

Such a device, an embodiment of which is shown in simplified manner in FIG. 5, is constituted by a stack of planar substrates $S_1$-$S_5$ having etched or molded patterns. The second duct 20 and the discharge duct(s) 40, 40' are formed by said etched or molded patterns at interfaces between substrates and parallel thereto. In contrast, the first duct 10 is constituted by a stack of through holes and it therefore passes through said substrates in substantially perpendicular manner.

Figure 6:
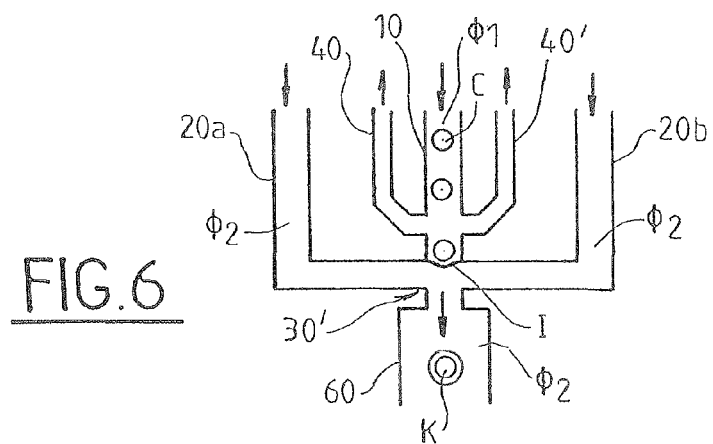
FIG. 6 shows a sixth embodiment of device of the invention.

In the embodiments of FIG. 1 to 5, the first and second ducts form a T-shaped type fluid junction 30 ("T-shaped" to be understood broadly since it is not essential for the two ducts to be mutually orthogonal). Nevertheless, this is not the only possible configuration. Thus, FIG. 6 shows a device in an alternative embodiment of the invention, based on using a microfluidic flow focusing junction 30'.

In this device, the second duct is constituted by two branches 20a and 20b that meet at the junction 30'. In these two branches, the second liquid phase $\phi_2$ flows towards said junction.

The fluidic junction 30' is not a three-branch junction like the T-junction 30 in FIGS. 1 to 3, but a four-branch junction: a third duct 60 is provided facing the first duct 10 for the purpose of receiving the oily phase coming from the branches 20a and 20b, and the particles C that are injected into the junction from the first duct.

The principle of microfluidic flow focusing (MFF) is known from the article by S. L. Anna, N. Bontoux, and H. A. Stone, "Formation of dispersions using 'flow focusing' in microchannels", Applied Physics Letters, 2003, 82(3): pp. 364-366.

Figure 7:
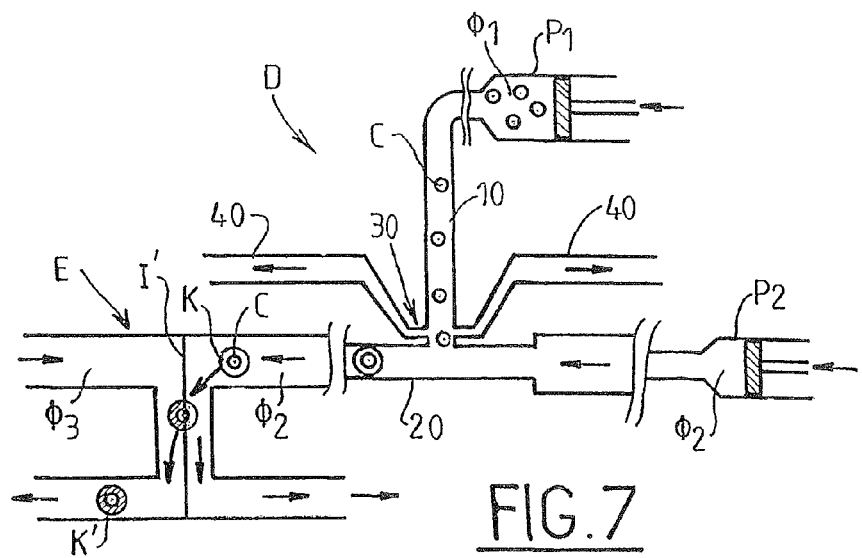
FIG. 7 is a diagram of a complete encapsulation system including a device as shown in any one of FIGS. 1 to 3, 5, or 6.

FIG. 7 is a diagram of a complete microfluidic system for encapsulating cells or cell clusters. Such a system comprises:
- a device D of the invention;
- injector means for injecting into the first duct 10 of said device a suspension made up of a first liquid phase $\phi_1$ and the particles for encapsulating; by way of example the injector means may comprise a syringe with a syringe-pusher P1 or a pressure controller;
- injector means for injecting the second liquid phase $\phi_2$ into the second duct 20 of the device, these injector means may likewise comprise a syringe with a syringe-pusher P2 or a pressure controller;
- optionally, suction means for sucking said first liquid phase via the discharge ducts 40, 40' (not shown; in a variant, the liquid may be discharged to the atmosphere); and
- microfluidic means E for gelling capsules; in the figure, reference K designates "capsules" that are not yet gelled, being constituted merely by cells or cell clusters surrounded by a film of the first liquid phase, whereas reference K' designates gelled capsules.

The microfluidic means E may be an H-shaped microfluidic device in which the second liquid phase $\phi_2$ comes into contact with an immiscible third liquid phase $\phi_3$ containing gelling agents in solution (e.g. $Ca^+$ ions when encapsulating with alginate). The capsules K pass through the interface I' between the second and third liquid phases, where they are subjected to a gelling reaction, and they are then recovered for implanting into a patient. Such a device is described in document US 2006/0051329. Document WO 2005/103106 describes another microfluidic gelling device suitable for use in combination with the encapsulating device of the invention.

The encapsulating device D and the gelling device E may be made in an integrated form (on a common substrate or stack of substrates) or they may be discrete.

It can be seen that the FIG. 7 system does not necessarily include a capsule sorting unit: this is due to the fact that the device D of the invention makes it possible to obtain capsules of dimensions and contents that are very uniform, and in particular makes it possible to avoid forming capsules that are empty. However, a device for sorting particles or clusters for encapsulating may advantageously be provided upstream from the encapsulating unit. Very numerous microfluidic sorting devices are known in the prior art; see for example documents WO 2004/037374, WO 2006/102258, WO 2002/02316, and the French patent application n° 0802575 entitled "Systeme microfluidique et procédé pour le tri d'amas de cellules et de préférence pour leur encapsulation en continue suite à leur tri" [A microfluidic system and method for sorting cell clusters, and preferably for continuously encapsulating them after sorting], in the name of the present Assignee and filed on May 13, 2008.

It is not always necessary for the gelling device to be present. Although it is generally essential when it is desired to obtain solid-walled capsules for implanting in a patient, there are circumstances (in particular in the field of research or biological analyses) in which it suffices to place the "encapsulated" cells or cell clusters in a droplet of liquid in suspension. Under such circumstances, the first liquid phase $\phi$ need not necessarily include an encapsulating agent.

What is claimed is:

1. A microfluidic device for controlled encapsulation of particles of sub-millimetric dimensions, or clusters of such particles, the device comprising:
    a first microfluidic duct for delivering a first liquid phase containing in suspension particles or particles clusters for encapsulating;
    a second microfluidic duct for conveying a flow of a second liquid phase that is immiscible with said first liquid phase; the first duct opening out into the second duct and forming a fluidic junction therewith;
    at least one discharge microfluidic duct for discharging the first liquid phase flowing in said first duct, being provided with a mouth disposed upstream from said junction and being suitable for being obstructed, at least in part, by a particle or particle cluster in suspension, thereby causing pressure to rise in the first duct;
    whereby particles or particle clusters entrained by said suspension along said first duct are liable to accumulate at said junction, being trapped at an interface between the two immiscible liquid phases, until they are injected into said second duct by the pressure rise caused by the mouth(s) of said discharge duct(s) being obstructed, wherein the device includes at least two discharge ducts or at least two pairs of discharge ducts having mouths situated at different distances from said junction, in which the section(s) of the mouths of said discharge ducts and the distance(s) of the mouths from the junction, and the section of the first duct, are selected in such a manner that a pressure sufficient for enabling a particle or particle cluster to be injected into the second duct is reached only when said at least two ducts or at least two pairs of ducts are obstructed, thereby making it possible to ensure that a plurality of particles or particle clusters are injected simultaneously.

2. A microfluidic device for controlled encapsulation of particles of sub-millimetric dimensions, or clusters of such particles, the device comprising:
    a first microfluidic duct for delivering a first liquid phase containing in suspension particles or particles clusters for encapsulating;
    a second microfluidic duct for conveying a flow of a second liquid phase that is immiscible with said first liquid phase; the first duct opening out into the second duct and forming a fluidic junction therewith;
    at least one discharge microfluidic duct for discharging the first liquid phase flowing in said first duct, being provided with a mouth disposed upstream from said junction and being suitable for being obstructed, at least in part, by a particle or particle cluster in suspension, thereby causing pressure to rise in the first duct;
    whereby particles or particle clusters entrained by said suspension along said first duct are liable to accumulate at said junction, being trapped at an interface between the two immiscible liquid phases, until they are injected into said second duct by the pressure rise caused by the mouth(s) of said discharge duct(s) being obstructed, wherein said first and second ducts present sections lying in the range 110% to 130% of the diameter d of the article to be encapsulated; said discharge duct(s) present sections of the order of 30% to 60% of the section of the first duct; and the distance(s) of the mouth(s) of said discharge duct(s) or pair(s) of discharge ducts from said junction lie(s) in the range 10% to 50% of the diameter of the article to be encapsulated.

3. A microfluidic device for controlled encapsulation of particles of sub-millimetric dimensions, or clusters of such particles, the device comprising:
    a first microfluidic duct for delivering a first liquid phase containing in suspension particles or particles clusters for encapsulating;
    a second microfluidic duct for conveying a flow of a second liquid phase that is immiscible with said first liquid phase; the first duct opening out into the second duct and forming a fluidic junction therewith;
    at least one discharge microfluidic duct for discharging the first liquid phase flowing in said first duct, being provided with a mouth disposed upstream from said junction and being suitable for being obstructed, at least in part, by a particle or particle cluster in suspension, thereby causing pressure to rise in the first duct;
    whereby particles or particle clusters entrained by said suspension along said first duct are liable to accumulate at said junction, being trapped at an interface between the two immiscible liquid phases, until they are injected into said second duct by the pressure rise caused by the mouth(s) of said discharge duct(s) being obstructed, wherein the device includes an array of micro-pillars at said or each mouth of said discharge duct(s).

4. A microfluidic device for controlled encapsulation of particles of sub-millimetric dimensions, or clusters of such particles, the device comprising:
    a first microfluidic duct for delivering a first liquid phase containing in suspension particles or particles clusters for encapsulating;
    a second microfluidic duct for conveying a flow of a second liquid phase that is immiscible with said first liquid phase; the first duct opening out into the second duct and forming a fluidic junction therewith;
    at least one discharge microfluidic duct for discharging the first liquid phase flowing in said first duct, being provided with a mouth disposed upstream from said junction and being suitable for being obstructed, at least in part, by a particle or particle cluster in suspension, thereby causing pressure to rise in the first duct;
    whereby particles or particle clusters entrained by said suspension along said first duct are liable to accumulate at said junction, being trapped at an interface between the two immiscible liquid phases, until they are injected into said second duct by the pressure rise caused by the mouth(s) of said discharge duct(s) being obstructed, wherein the device includes an array of micro-pillars at the fluidic junction between the first and second ducts.

* * * * *